United States Patent
Shah et al.

(10) Patent No.: US 7,628,998 B2
(45) Date of Patent: Dec. 8, 2009

(54) COLORED COSMETIC COMPOSITIONS WITH PEARLESCENT AND COLOR PIGMENT BLENDS

(75) Inventors: Arvind N. Shah, Suffern, NY (US); Ernest S. Curtis, Milford, PA (US)

(73) Assignee: Avon Products, Inc., New York, NY (US)

( * ) Notice: Subject to any disclaimer, the term of this patent is extended or adjusted under 35 U.S.C. 154(b) by 196 days.

(21) Appl. No.: 10/622,299

(22) Filed: Jul. 18, 2003

(65) Prior Publication Data

US 2004/0018161 A1    Jan. 29, 2004

Related U.S. Application Data

(60) Provisional application No. 60/397,291, filed on Jul. 19, 2002.

(51) Int. Cl.
*A61K 8/02* (2006.01)
*A61Q 1/02* (2006.01)
*A61K 31/01* (2006.01)

(52) U.S. Cl. .................. 424/401; 424/63; 424/70.12; 514/844; 514/762

(58) Field of Classification Search ............ 424/63, 424/401, 70.12; 514/844, 762
See application file for complete search history.

(56) References Cited

U.S. PATENT DOCUMENTS 3,647,492 A * 3/1972 Chapman et al. ............ 106/418
5,800,816 A * 9/1998 Brieva et al. ................ 424/63
6,117,435 A   9/2000 Painter et al.
6,372,202 B1  4/2002 Simon
6,395,262 B1  5/2002 Favre et al.
6,511,672 B2 * 1/2003 Tan et al. .................... 424/401

FOREIGN PATENT DOCUMENTS

WO    00/51551 A2    9/2000
WO    02/056846 A1   7/2002

OTHER PUBLICATIONS

Nishikata, et al. "A Natural-Looking Makeup" Cosmetics & Toiletries magazine vol. 112, May 1997, p. 39-56.

* cited by examiner

*Primary Examiner*—Sreeni Padmanabhan
*Assistant Examiner*—Kantamneni Shobha
(74) *Attorney, Agent, or Firm*—Joan M. McGillycuddy; Charles S. Zeller; Anthony M. Santini

(57) ABSTRACT

There is provided compositions and methods for providing a natural appearance, healthy glow, and other aesthetic benefits to the skin. One composition has a shade-matched pearlescent component. Another composition has a blend of a shade-matched pearlescent component and a shade-matched pigment component. Preferably, the blend is incorporated into an emulsion, a powder, cream-to-powder cosmetic, a gel, a pomade, a solution, a stick, suspension, or a wet/dry foundation.

20 Claims, No Drawings

COLORED COSMETIC COMPOSITIONS WITH PEARLESCENT AND COLOR PIGMENT BLENDS

CROSS REFERENCE TO RELATED APPLICATIONS

The present application is claiming priority of U.S. Provisional Application Ser. No. 60/397,291 filed on Jul. 19, 2002, the disclosure of which is hereby incorporated in its entirety by reference.

BACKGROUND OF THE INVENTION

1. Field of the Invention

The present invention relates to cosmetic compositions. In one embodiment, the invention relates to cosmetic compositions having a shade-matched pearlescent component. In a preferred embodiment, the invention relates to cosmetic compositions having both a shade-matched pearlescent component and a pigment component that are blended together to form a cosmetic composition that, when applied topically to the skin, provides a translucent natural appearance and a healthy glow. The present invention also relates to a method for imparting these benefits as well as a method for making these compositions.

2. Description of the Prior Art

It is generally accepted that beautiful skin has a transparent quality with uniform undertones of color. The basis for this attractive, natural-looking appearance is skin structure. This appearance is influenced by a number of factors.

The outer layer of human skin is a semi-transparent layer known as the stratum corneum. Underlying the stratum corneum is a layer of skin that has the blood vessels and pigments of the body. The reddish hue of the blood vessels, hemoglobin, and the brown/black hue of melanin combine to produce, through the transparency of the stratum corneum, the skin's color. Color cosmetic manufacturers know that matching the skin tone/color is important to provide a desirable cosmetic product, especially foundation make-up compositions. A foundation cosmetic or make-up composition is often used to provide a uniform "base" of skin color onto which is applied other colored cosmetics, such as a blush. A user prefers a foundation cosmetic that not only matches his/her skin color but that also gives his/her skin an even, natural or healthy glow.

The importance of using pigments to match colored cosmetics to the skin color/tone of the consumer is known. However, there has been a need for a foundation cosmetic that does not give the user a "made-up" look, but instead provides a natural translucent sheen, i.e. healthy glow, and natural color. It is difficult, however, to have a foundation cosmetic that covers both flaws in the skin, as well as uneven skin tone, yet still provides the vibrant healthy glow of clean, bare skin. The primary reason for this difficulty is that the components of such compositions that provide the desired color and coverage, such as the titanium or iron oxide pigments, are largely opaque, and therefore obscure the desired vibrant transparency of natural looking skin. In fact, such components often impart a whitish, chalky appearance to lighter skin, and an ashy look to darker skin. Such a whitish, chalky skin appearance is especially evident under certain light conditions, such as fluorescent, ultraviolet and even natural light. Pigments, such as titanium oxide and iron oxides, are frequently used in products such as bronzers that provide a deeper color and a sunned or tanned appearance. However, such compositions are not intended to match the natural skin tone and do not enhance the natural color and glow of the skin. Additionally, even though transparent pigments have recently become available, a cosmetic composition that provides the desired aesthetic appearance of translucent natural sheen has not yet been achieved.

Also, color pigments that are typically used to match skin tone to the natural color of the skin, often cannot achieve the natural sheen (healthy glow) of bare, healthy, youthful skin and, moreover, often provide a dull matte look. Commercial products have incorporated pearlescent ingredients to impart sheen, but these pearlescent ingredients (e.g., one color silver or gold-toned reflectance pearls) often give an unnatural/artificial shiny/glittery look to the skin.

Commercial foundation formulas have also attempted to provide the appearance of healthy glowing skin by including emollient ingredients that impart shine to the skin. However, any benefits achieved by these compositions change over time due to various factors (e.g., the composition wipes off or moves on the skin, or changes due to the secretion of sebum).

Clearly, there are competing factors in the development of a natural-looking makeup that, heretofore, have been extremely difficult, if not impossible to resolve.

Very recently, the cosmetics industry has used a detailed study of the optics of light absorption, reflection and scattering in the skin to attempt to design a product that, when applied to the skin, will convey to the viewer the impression of a natural but flawless clean skin (See, for example, Nishikata et al., Cosmetics and Toiletries 112:39-55, 1997). It is now recognized that the angle of viewing of the skin will alter the appearance to the viewer. For example, the viewer will see more of the red of hemoglobin in the skin's dermis when the skin is viewed at virtually a perpendicular angle. However, the viewer will see more brown, due to the melanin content of the outer layers of epidermis when the skin is viewed at an acute angle.

There have been attempts to understand the optical events leading to a viewer's perception of natural-looking skin by the use of diffuser type ingredients. For example, U.S. Pat. No. 6,117,435 to Painter et al. describes a composition that includes silica beads and an interference pigment. While such optical diffusers, reflectors, and refractors tend to provide the impression of skin having an even landscape, i.e., less wrinkles and lines, they also result in a dull, blurred masked appearance, and fail to provide the desired natural, healthy glow.

The present invention provides unique cosmetic compositions and methods of making such cosmetic compositions that provide desired skin tone, namely natural sheen and natural color, and that, when applied, provide the skin with a natural, healthy glow as well as other aesthetic benefits.

SUMMARY OF THE INVENTION

It is an object of the present invention to provide a composition that provides a natural appearance and healthy or natural glow when applied to the skin.

It is another object of the present invention to provide a composition that provides even coverage.

It is yet another object of the present invention to provide a composition that provides even coverage and an illusion of sheerness.

It is still another object of the present invention to provide a composition that provides a transparent look or appearance when applied to the skin.

It is yet still another object of the present invention to provide a composition that provides a translucent appearance on the skin that imitates the sheen of natural skin.

It is even yet another object of the present invention to provide a composition that provides a combination of transparency and translucence so that the skin has a youthful, healthy, natural, yet luminous, appearance.

It is a further object of the present invention to provide a composition that avoids an ashy, chalky or opaque hue to the skin even when the skin is viewed from different angles.

It is still a further object of the present invention to provide a method for imparting one or more of the following attributes: a natural appearance, healthy or natural glow or appearance, transparent appearance, translucent appearance, or luminous appearance.

It is an additional object of the present invention to provide a method for preparing a cosmetic composition that provides a natural appearance and healthy glow when applied to the skin.

These and other objects and advantages of the present invention are achieved by a composition having a pearlescent component that is initially matched to a benchmark that has a desired skin tone. Preferably, the composition has a blend of a pearlescent component and a pigment component that are each separately matched to a single benchmark of natural skin tone and color. The pearlescent component preferably has a bismuth oxychloride-based pearlescent ingredient. Such a pearlescent ingredient preferably is a combination of colored pigment bonded to bismuth oxychloride and mica using calcium stearate. The pigment component can include many known pigments.

The blend of the pearlescent component and the pigment component is present in an amount effective to provide benefits including, sheerness, even coverage, natural glow, transparent appearance, translucent appearance, and luminous appearance. The blend is generally present in an amount about 0.01 wt % to about 50 wt % based on the total weight of the composition.

Other embodiments of the present invention are directed to a composition, method of making the composition, and method of using the composition, that has a shade-matched pearlescent component. The compositions of the present invention can be in the form of an emulsion (e.g., water-in-oil, oil-in-water, silicone-in-water, water-in-silicone and triple, O/W/O or W/O/W, emulsions), a powder (either pressed or loose), a cream-to-powder cosmetic product, a gel, a pomade, a solution, a stick, a suspension, or a wet/dry foundation. Preferably, the composition, particularly when it is intended for use as a foundation, is in the form of an emulsion. More preferably, the composition is in the form of a water in silicone emulsion or silicone in water emulsion. Most preferably, the composition is in the form of a water in silicone emulsion. Preferably, the composition also has isododecane, most preferably in the silicone or oil phase. Optimally, isododecane is present in an amount about 25 wt % to 75 wt %, based upon the total weight of the silicone or oil phase.

The present invention also includes methods for imparting a natural appearance and a healthy glow to the skin. The methods include applying to the skin the above compositions, preferably in an amount effective to achieve a visual impression of a natural appearance and/or a healthy glow to the skin. The present invention further includes methods for imparting to the skin other desirable attributes. These attributes include, an illusion of sheerness, even coverage, natural glow, transparent appearance, translucent appearance, and luminous appearance. These attributes are achieved by applying to the skin an amount of the above composition effective to achieve visually one or more of the above attributes.

The present invention additionally includes a method for preparing a cosmetic composition for topical application to the skin. The method includes shade-matching a pearlescent component to a natural skin tone benchmark shade to form a shade-matched pearlescent component. In a preferred embodiment, the method includes separately shade-matching a pigment component to the natural skin color benchmark shade to form a shade-matched pigment component, forming a shade-matched blend having the shade-matched pigment component and the shade-matched pearlescent component, and incorporating the shade-matched blend into a cosmetic carrier.

A particularly advantageous aspect of the present invention is that, once formed, the shade-matched pearlescent component may be added to prior art foundation compositions to transform such prior art compositions into compositions that provide the aesthetically pleasing, heretofore unavailable benefits of the present invention.

Other and further objects, advantages and features of the present invention will be understood by reference to the following.

DESCRIPTION OF THE INVENTION

The present invention provides a cosmetic composition that includes a shade-matched pearlescent component. In a preferred embodiment, the composition also includes a shade-matched pigment component.

In another preferred embodiment, the composition has a blend of a pearlescent ingredient or component and a pigment ingredient or component, preferably in a vehicle. The pearlescent component matched to skin tone and the pigment ingredient matched to skin color are separately shade-matched to a single natural skin tone benchmark or shade prior to incorporation into the blend. In production, significantly, the pearlescent component is first separately shade-matched and then is added to the remainder of the composition at any time in the formulation process. In fact, as will be further explained below, the shade-matched component can be added to prior art color cosmetic foundation-like composition just before or just after the prior art color cosmetic foundation-like composition is applied to the skin.

Shade matching of color cosmetic composition using pigments is known to those of ordinary skill in art of color cosmetics. In known shade matching, a shade of color (such as a skin color) is selected as a "benchmark" and ingredients (usually the pigment component) are added and/or adjusted to match the shade of the "benchmark". What the present invention has discovered is that when this known art of pigment shade-matching is also used to shade-match a separate pearlescent component to skin color, the resultant colored cosmetic mimics healthy skin's natural glow more accurately than any heretofore commercial colored cosmetic product. This is especially true for any known foundation cosmetics products.

A significant feature of the present invention is that the pearlescent component is matched to the desired natural skin tone (hereinafter "benchmark shade") rather than simply added as an accent to a shade-matched pigment component, as has been done in the prior art. The shade-matched pearlescent component may include any color-based pearls or any combinations thereof. The pearlescent component can be matched to the desired natural skin tone benchmark shade according to any known shade-matching method known in the art or by using the method noted above.

Preferably, the pearlescent component has a bismuth oxychloride based pearlescent ingredient or reflectance pearls. Bismuth oxychloride matches the skin's natural pearlescence more than compounds such as titanium oxide, which provide for a more artificial look. Bismuth oxychloride better mimics the skin's natural reflectance. However, other pearlescent ingredients may be used. A preferred pearlescent component is called CHROMA-LITE, which is a combination of colored pigment bonded to BI-LITE 20 (bismuth oxychloride and mica) using calcium stearate. The CHROMA-LITE component is available in various shades/color from Englehard Corporation (Iselin, N.J.).

The pigment component may include any known pigment. However, D&C and FD&C approved pigments are particularly preferred. Most preferred are US FDA approved pigments.

Known pigments include mineral pigments. Representative mineral pigments that can be used in the present invention include, for example, titanium dioxide (rutile or anatase) optionally surface treated and listed in the Color Index under reference CI 77891; black, yellow, red and brown iron oxides listed in Color Index under references CI 77499, 77492 and 77491; manganese violet (CI 77742); ultramarine blue (CI 77007); chromium oxide (CI 77288); hydrated chromium oxide (CI 77289); ferric blue (CI 77510), or any combinations thereof.

Additional exemplary color additive lakes include, for example: D&C Red No. 19 (e.g., CI 45170, CI 73360 or CI 45430); D&C Red No. 9 (CI 15585); D&C Red No. 21 (CI 45380); D&C Orange No. 4 (CI 15510); D&C Orange No. 5 (CI 45370); D&C Red No. 27 (CI 45410); D&C Red No. 13 (CI 15630); D&C Red No. 7 (CI 15850:1); D&C Red No. 6 (CI 15850:2); D&C Yellow No. 5 (CI 19140); D&C Red No. 36 (CI 12085); D&C Orange No. 10 (CI 45475); D&C Yellow No. 19 (CI 15985); FD&C Red #40 (CI# 16035); FD&C Blue #1 (CI# 42090); FD&C Yellow #5 (CI# 19140); or any combinations thereof. Most preferably, the lakes are certified by the US FDA. Natural colorants, such as carmine, may also be used.

Other pearls are white nacreous materials, such as mica covered with titanium oxide or covered with bismuth oxychloride; and colored nacreous materials, such as titanium mica with iron oxides, titanium mica with ferric blue or chromium oxide, titanium mica with an organic pigment of the aforementioned type. However, these other materials sometimes lend a white, chalky, ashy appearance to the skin when the final composition is applied to the skin, and thus these materials are preferably not used in the present invention. Furthermore, if they are used, it is preferred that these materials are used in an amount of less than 1.0 wt %.

Colored cosmetic compositions of the present invention may have any ratio of shade-matched pearlescent component to shade-matched pigment component. However, the blend of the two shade-matched components is about 0.01 percent by weight (wt %) to about 50 wt %, and more preferably about 0.05 wt % to about 25 wt %, based on the total weight of the cosmetic composition. Most preferably, the shade-matched blend is about 1 wt % to about 25 wt % based on the total weight of the cosmetic composition.

As mentioned above, a particularly advantageous aspect of the present invention is that, once formed, the shade-matched pearlescent component may be added to prior art foundation compositions to transform such prior art compositions into compositions that provide the aesthetically pleasing, heretofore unavailable benefits of the present invention. The benefit of the present invention is that the shade-matched pearlescent component may be added to the prior art composition either before or after the prior art composition is applied to the skin.

EXAMPLE 1

Emulsion Composition

An example of an emulsion composition, which is a foundation composition, according to the present invention is as follows. A shade-matched pearlescent component and a shade-matched pigment component are individually formed. The pearlescent component is separately shade-matched first. The shade-matched pearlescent component and shade-matched pigment component are then blended to form a shade-matched blend. The shade-matched pearlescent component may be added at any time during the process.

The shade-matched blend preferably is about 0.01 wt % to about 25 wt % based on the total weight of the foundation or emulsion composition. More preferably, the shade-matched blend is about 0.05 wt % to about 20 wt % based on the total weight of the foundation or emulsion composition. Most preferably, the shade-matched blend is about 0.075 wt % to about 15 wt % based on the total weight of the foundation or emulsion composition.

EXAMPLE 2

Stick Composition

An example of a stick composition, which is a concealer composition, according to the present invention is as follows. As in Example 1, a shade-matched pearlescent component and a shade-matched pigment component are individually formed. The shade-matched pearlescent component and shade-matched pigment component are then blended to form a shade-matched blend. The shade-matched blend is then incorporated into a vehicle or the concealer composition, as discussed above in Example 1.

Preferably, the shade-matched blend is about 0.01 wt % to about 25 wt % based on the total weight of the final concealer, or any stick composition. More preferably, the shade-matched blend is about 1 wt % to about 20 wt % based on the total weight of the concealer composition. Most preferably, the shade-matched blend is about 2.5 wt % to about 15 wt % based on the total weight of the concealer composition.

EXAMPLE 3

Powder-Type Foundation Composition

An example of a powder-type composition, also a foundation composition, according to the present invention is as follows. Again as in Example 1, a shade-matched pearlescent component and a shade-matched pigment component are individually formed. The shade-matched pearlescent component and shade-matched pigment component are then blended to form a shade-matched blend. The shade-matched blend is then incorporated into a vehicle or the powder-type composition as discussed above in Example 1.

The shade-matched blend preferably is about 0.01 wt % to about 25 wt % based on the total weight of the powder-type or foundation composition. More preferably, the shade-matched blend is about 0.5 wt % to about 15 wt % based on the total weight of the composition. Most preferably, the shade-matched blend is about 1.5 wt % to about 12 wt % based on the total weight of the composition.

In addition to the product forms discussed above (emulsion, powder, and stick), the present invention may be used to provide improved colored cosmetic compositions to all types of cosmetics, including, but not limited to, pressed and/or loose powders, cream to powder cosmetic products, gel, pomades, solutions, suspensions and wet/dry foundations. Preferably, the composition is in the form of a water in silicone emulsion, or silicone in water emulsion. Most preferably, the composition is in the form of a water in silicone emulsion. Preferably, the composition also has isododecane. Optimally, isododecane is present in an amount about 25 wt % to about 75 wt % based on the total weight of the silicone phase.

Significantly, these compositions provide the same or virtually the same visual appearances no matter the angle from which the wearer of the composition is viewed.

The present invention further provides methods of making such a cosmetic composition. A second, preferred method includes shade-matching a pearlescent component to a natural skin tone benchmark shade to form a shade-matched pearlescent component; separately shade-matching a pigment component to the natural skin tone benchmark shade to form a shade-matched pigment component; forming a shade-matched blend having the shade-matched pigment component and the shade-matched pearlescent component; and incorporating the shade-matched blend into a cosmetic carrier. After the pearlescent component is shade-matched, it may be incorporated into the composition at any time.

The present invention having been described with particular reference to the preferred forms thereof, it will be obvious that various changes and modifications may be made herein without departing from the spirit and scope of the invention as defined in the appended claims.

What is claimed is:

1. A composition for topical application to the skin comprising:
   a pearlescent component comprising a bismuth oxychioride-containing pearlescent ingredient bonded to a colorant with calcium stearate, wherein said pearlescent component matches in shade a natural skin tone benchmark shade;
   a pigment component that also matches in shade said benchmark shade, wherein said pigment component does not comprise a nacreous material; and
   a cosmetic carrier;
   wherein said pearlescent component and said pigment component form a blend present in an amount of about 0.01 wt % and about 50 wt % based on the total weight of the composition.

2. The composition of claim 1, wherein said blend is present in an amount about 0.05 wt % to about 25 wt % based on the total weight of the composition.

3. The composition of claim 1, wherein said blend is present in an amount about 1 wt % to about 25 wt % based on the total weight of the composition.

4. The composition of claim 1, wherein said blend is present in an amount effective to provide at least one benefit selected from the group consisting of an illusion of sheerness, even coverage, natural glow, healthy glow, transparent appearance, translucent appearance, luminous appearance, and any combinations thereof.

5. The composition of claim 1, wherein the composition is in a form selected from the group consisting of an emulsion, a powder, a cream-to-powder cosmetic, a gel, a pomade, a solution, stick, suspension, a wet/dry foundation, and any combinations thereof.

6. The composition of claim 5, wherein the composition is in the form of an emulsion.

7. The composition of claim 6, wherein the composition is in the form of a water in silicone emulsion.

8. The composition of claim 7, wherein said water in silicone emulsion comprises a silicone phase having isododecane.

9. The composition of claim 8, wherein said isododecane is present in an amount about 25 wt % to about 75 wt % based on the total weight of the silicone phase.

10. A foundation composition comprising the composition of claim 6.

11. A method for preparing a cosmetic composition for topical application to the skin comprising:
    shade-matching a pearlescent component comprising a bismuth oxychioride-containing pearlescent ingredient bonded to a colorant with calcium stearate, to a natural skin tone benchmark shade to form a shade-matched pearlescent component;
    shade-matching a pigment component to said benchmark shade to form a shade-matched pigment component, wherein said pigment component does not comprise nacreous material;
    blending said shade-matched pearlescent component and said shade-matched pigment component to form a shade-matched blend; and
    adding said shade-matched blend to a cosmetic carrier to form a cosmetic composition;
    wherein said shade-matched blend is present in an amount of about 0.01 wt % to about 50 wt % based on the total weight of the composition.

12. The method of claim 11, wherein said blend is present in an amount about 0.05 wt % to about 25 wt % based on the total weight of the composition.

13. The method of claim 11, wherein said blend is present in an amount about 1 wt % to about 25 wt % based on the total weight of the composition.

14. The method of claim 11, wherein said blend is present in an amount effective to provide at least one benefit selected from the group consisting of an illusion of sheerness, even coverage, natural glow, healthy glow, transparent appearance, translucent appearance, luminous appearance, and any combinations thereof.

15. The method of claim 11, wherein the composition is in a form selected from the group consisting of an emulsion, a powder, a cream-to-powder cosmetic, a gel, a pomade, a solution, stick, suspension, a wet/dry foundation, and any combinations thereof.

16. The method of claim 15, wherein the composition is in the form of an emulsion.

17. The method of claim 16, wherein the composition is in the form of a water in silicone emulsion.

18. The method of claim 17, wherein said water in silicone emulsion comprises a silicone phase having isododecane.

19. The method of claim 18, wherein said isododecane is present in an amount about 25 wt % to about 75 wt % based on the total weight of the silicone phase.

20. The method of claim 16, wherein said composition is a foundation composition.

* * * * *